US009872867B2

(12) United States Patent
Kuritz (10) Patent No.: US 9,872,867 B2
(45) Date of Patent: Jan. 23, 2018

(54) METHODS AND COMPOSITIONS FOR MODULATION OF INNATE IMMUNITY (76) Inventor: Tanya Kuritz, Kingston, TN (US)

( * ) Notice: Subject to any disclaimer, the term of this patent is extended or adjusted under 35 U.S.C. 154(b) by 1531 days.

(21) Appl. No.: 12/157,088

(22) Filed: Jun. 6, 2008

(65) Prior Publication Data

US 2009/0306017 A1 Dec. 10, 2009

(51) Int. Cl.
A61K 31/66 (2006.01)

(52) U.S. Cl.
CPC .................................. A61K 31/66 (2013.01)

(58) Field of Classification Search
CPC .............................. A61K 31/661; A61K 31/66
See application file for complete search history.

(56) References Cited

U.S. PATENT DOCUMENTS

| 4,059,641 A | 11/1977 | Mishima et al. | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 6,525,035 B1 | 2/2003 | Danilov et al. | |
| 6,911,434 B2 | 6/2005 | Baldridge et al. | |
| 2002/0064501 A1* | 5/2002 | Khan | A61K 38/07 424/9.2 |
| 2003/0206886 A1* | 11/2003 | Lattime | C07K 16/244 424/93.2 |
| 2007/0059319 A1* | 3/2007 | Carlson | A61K 31/165 424/185.1 |

FOREIGN PATENT DOCUMENTS

| EP | 0166436 A2 | 1/1986 |
|---|---|---|
| EP | 0350801 A2 | 1/1990 |
| RU | 2129867 C1 | 5/1999 |
| RU | 2177788 C2 | 1/2002 |

OTHER PUBLICATIONS

Netea et al. (Antimicrobial Agents and Chemotherapy, vol. 49, No. 10, pp. 3991-3996; Oct. 2005).*
Trinchieri (Nature Reviews: Immunology, vol. 3, "abstract"; Feb. 2003).*
Imanishi et. al., Journal of Immunology, 2007, The American Association of Immunologists, vol. 178, pp. 6715-6719.*
Rutkowski et. al., Central-European Journal of Immunology, 1999, Official Journal of the Polish Society of Experimental and Clinical Immunology, vol. 24, pp. 299-305.*
Lewis, R.S. Biochem. Soc. Trans. 31 (2003): 925-929.
Lauzon et al., Adv Exp Med Biol. 598 (2007): 1-11.
2006 Wickelgren, Science, 2006; 312:184-187.
Medzhitov et al., Nature, 1997, vol. 388, 394-397.
Janeway and Medzhitov, Annu. Rev. Immunol., 2002, vol. 20, 197-216.
Bendelac and Medzhitov, J. Exp. Med., 2002, F19-F23, vol. 195, No. 5.
Caramalho et al., J. Exp. Med., 2003, 403-411, vol. 197, No. 4.
Xu et al., Cell. Immunol., 2005, 85-89, vol. 233.
Krishnan et al., Exper. and Mole. Med., 2007, 421-438, vol. 39, No. 4.
Roach et al., PNAS, 2005, 9577-9582, vol. 102, No. 27.
Heil et al., Science, 2004, 1526-1529, vol. 303.
Nishiya and DeFranco, J. Biol. Chem., 2004,19008-19017, vol. 279, No. 18.
Ismaili, et al., J. Immunol., 2002, 926-932, vol. 168.
Lilienbaum and Israel, Mol. Cell. Biol., 2003, 2680-2698, vol. 23, No. 8.
Mogensen, et al., J. Immunol., 2003, 6224-6223, vol. 170.
Pasterkamp, et al., Eur J. Clin Investi, 2004, 328-334, vol. 34.
Stover, et al., J. Biol. Chem., 2004, 4440-4449, vol. 279, No. 6.
Isogawa, et al., J. Virol., 2005, 7269-7272, vol. 79, No. 11.
Patel, et al., J. Immunol., 2005, 7558-7563, vol. 174.
Cox and Der, Biochim Biophy Acta 1333, 1997, F51-F71.
Levy et al, Nature, 1997, 985-990, vol. 389.
Morita, et al, 1999, Microbes Infect., 1999, 175-186.
Morita et al., J. Immunol. 167 (2001): 36-41.
Pronin et al., Russ J. Immunol. 5, No. 2 (2000): 156-164.
Moody et al., Nature 404 (2000): 884-888.
Moody, Cell. Mol. Life Sci. 58 (2001): 1461-1474.
Roura-Mir et al., J. Immunol. 175 (2005): 1758-1766.
Behera et al., J. Biol Chem. 277, No. 28 (2002): 25601-25608.
Tilles et al., Pro Soc Exper Biol Med. 186 (1987): 70-74.
Plescia et al., Proc Nat Acad Sci, USA 72, No. 3 (1975): 888-891.
Zhang et al., J. Immunology 165 (2000): 1762-1770.
Schnurr et al., Blood 105 (2005): 1582-1589.
Hawiger et al., Blood 94, No. 5 (1999): 1711-1716.
Jones et al., Inf Immunity 71, No. 5 (2003): 2626-2633.
Oliveira et al., Mem Inst Oswaldo Cruz, Rio de Janeiro 96, No. 7 (2001): 973-978.
Schaefer et al., J. Clin Invest. 115, No. 8 (2005): 2223-2233.
Del Prete. Intern Rev Immunol. 16 (1998): 427-455.
Tausk et al., Dermatol Ther. 21 (2008): 22-31.
Elkarmi and Hamad, Biol Forum 100 (2007): 405-424.
Krishnan et al., Exper Mol Med. 39, No. 4 (2007): 421-438.
Hemming, Proceedings of the Biochemical Society, Biochem J. 113 (1969): 23p-25p.
Prenol Nomenclature (1986) International Union of Pure and Applied Chemistry and International Union of Biochemistry: www.chem.qmul.ac.uk/iupac/misc/prenol.html.

(Continued)

Primary Examiner — Sarah Pihonak (57) ABSTRACT

The present invention is directed towards a method of modulation of the innate immune of an organism system with the phosphorylated polyprenols of the present invention. The present invention is also directed towards a method of activation and/or modulation of the Toll-like Receptors with the phosphorylated polyprenols of the present invention. The present invention is also directed towards compound(s) comprising C35-C90 polyisoprenyls of Formula 1 and Formula 2 and their derivatives as well as methods of use of including activation and/or modulation of TLRs including TLR-2 and TLR-4 receptors and uses thereof including, e.g., use as antimicrobial, immunoregulatory, anti-cancer, for control of inflammatory conditions and as vaccine adjuvants.

16 Claims, 4 Drawing Sheets (56) References Cited

OTHER PUBLICATIONS

Maltsev et al., Russian Journal of Biological Chemistry 27, No. 6 (2001): 449-452.
Rudney, Proceedings of the Biochemical Society, Biochem. J. 128 (1972): 13p-14p.
Fairlamb et al., Bioorg. Chemistry 31 (2003): 80-97.
V.N. Shibaev and L.L. Danilov. Biochem Cell Biol. 70 (1992): 429-437.
Danilov, L.L. and Shibaev, V.N. Studies in Natural Products Chemistry 8(1991): 63-114.
Chojnacki and Vogtman, Acta Biochimica Polonica 31, No. 1, (1984): 115-126.
Guha and Mackman, Cell. Signalling 13 (2001): 85-94.
Lagoumintzis et al., Inf Immunity 71 No. 8, (2003): 4614-4622.
Baqui et al., Oral Microbiol Immunol., 14 (1999): 275-280.
Murthy et al., Inf Immunity 68 No. 12, (2000): 6663-6669.
D'Aquisto et al. (2007) Blood 109 (3): 1095-1102.
Huppa et al. (2003) Nature Immunol. 4 (8): 749-755.
Koncz et al. (2007) J. Immunol. 179: 6613-6619.
Murphy et al. (1995) Mol. Cell. Biol. 15(10): 5258-5267.
Shigematsu et al. (2007) J. Radiat. Res. 48(1): 51-55.
Smith-Garvin et al. (2009) Annu. Rev. Immunol. 27: 591-619.
Yamamoto et al. (2007) Immunology 121: 383-391.
Gahring et al. (1985) J Clin Invest. 76:1585-1591.
Krueger et al. (2007) Sleep Med Clin. 2: 161-169.
Popa et al. (2007) J. Lipid Res. 48: 751-762.
Wickelgren (2006) Science 312: 184-187.

\* cited by examiner

METHODS AND COMPOSITIONS FOR MODULATION OF INNATE IMMUNITY

FIELD OF THE INVENTION

The present invention relates to application of compositions for the modulation of Toll-like-receptor (TLR)-mediated immune response.

BACKGROUND OF THE INVENTION

Despite significant progress in drug discovery there is still a lack of effective therapies for a number of cancers, inflammation-linked diseases, viral diseases, or allergies. The immune response is a common factor for all these pathologies (Wickelgren, 2006, Science, 312: 184-187) and, therefore, provides a target for new drug discovery. Stimulation of immunity is also beneficial in promoting better responses to vaccines (adjuvants) and to control lipid and carbohydrate metabolism. Compositions that stimulate and modulate immune responses have a promise as medicines and adjuvants for use against a number of diseases.

Research in the past decade led to the discovery of Toll-like receptors (TLR) which were shown to play a major role in immune response to microbial infections (Medzhitov et al., 1997, Nature, 388: 394-397, Janeway & Medzhitov, 2002, Annu. Rev. Immunol. 20: 197-216, Bendelac & Medzhitov, 2002, J. Exp. Med, 195: F19-F23). The function of TLR receptors was demonstrated to the modulation of innate immunity (i.e., non-adaptive immunity) which acts as a system of defense for organisms against pathogens by launching of an inflammatory response. These receptors are activated upon recognition of pathogen-associated molecular patterns (PAMPs) (Carmalho et al., 2003, J. Exp. Med. 4: 403-411, Xu et al., 2005, Cell Immunol, 233, 85-89).

Physiological molecular mechanisms of induction of immune responses have been partially described for the currently known thirteen TLRs (Krishnan, et al., Exp Mol Med, 38:421-438, 2007; Roach, et al, PNAS, USA 102: 9577-9582, 2005; Janeway & Medzhitov, 2002, Annu. Rev. Immunol. 20: 197-216, Heil et al., 2004, Science, 303: 1526-1529, Nishiya & DeFranco, 2004, J. Biol. Chem. 279: 19008-19017). TLR-4 and TLR-2 were shown to interact with CD14 and lead to dendritic cell (DC) maturation (Ismaili et al., 2002, J. Immunol., 168: 926-932) and NF-κB activation through mechanisms triggered by calcium signaling (Lilienbaum and Israel, 2003, Mol. Cell. Biol. 23: 2680-2698, Mogensen, et al., 2003, J. Immunol. 170: 6224-6233).

Among TLR-2 and TLR-4 agonists, the most studied are natural lipopolysaccharides (LPS) from cell walls of Gram-negative bacteria. Other known TLR-4 agonists include lipoteichoic acids of Gram-positive bacteria, Protein F of respiratory syncytial virus, Taxol from plants, HSP60 from bacteria, EDA in fibronectin and hyaluronan produced by hosts (Pasterkamp, et al., 2004, Eur J Clin Invest, 34: 328-334). Lately, with the development of synthetic monophosphoryl lipid A (MPL), a TLR-4 agonist (Stover, et al., 2003, J. Biol. Chem, 279: 4440-4449), a number of studies appeared on the utility of the synthetic compound for treatment and prevention of infectious diseases (Baldridge, et al., 2005, U.S. Pat. No. 6,911,434; Isogawa, et al., 2005, J. Virol., 79: 7269-7272) and allergic airway inflammation (Patel, et al., 2005, J. Immunol. 174:7558-7563).

Phosphorylated polyprenols have been offered as an agent for upregulating Th1-mediated immunity in living organisms and this application has been patented (Danilov, et al., 2003, U.S. Pat. No. 6,525,035). Cox and coworkers also reported criticality of C15 farnesyl isoprenoid group for cell signaling in the Ras pathway through farnesylation of signal proteins (Cox and Der, 1997, Biochim Biophys Acta, 1333: F51-F71). Polyisoprenyl phosphates were shown to play an important role in intracellular signaling through inhibiting of superoxide anion production in neutrophils (Levy, et al., 1997, Science, 389: 985-990). Morita, et al., (1999, Microbes Infect, 1: 175-186) showed that short, C5-C20 prenyl pyrophosphates may serve as antigens, the recognition of which is conserved in vertebrate evolution of γδ T cells. They later offered a potential model of prenyl antigen interaction with T-cell receptors (TCR, Morita, et al., 2001, J. Immunol, 167: 36-41). Those suggestions are in-line with earlier findings that the compounds of our prior patent protect organisms from viral infections (Danilov, et al., 2003, U.S. Pat. No. 6,525,035), that derivatives of shorter polyprenols may have direct antimicrobial effects (Fairlamb, et al., 2003) and that phosphorylated polyprenyls lacked ability to induce cytokines on their own and needed a co-inducers such as viruses, etc (Pronin, et al., 2000). However, despite results pointing to the potential significance of those compounds in cell signaling, cellular targets for 1,4-cis-polyprenyl phosphoryl derivatives have not been identified.

Naturally occurring glycosylated polyisoprenols isolated (purified components of defined structures) from the cell wall of *Mycobacterium tuberculosis* were shown to be presented by the CD1c protein and recognized by the T-cell antigen receptors (TCRs) (Moody, et al., 2000, Nature, 404: 884-888; Moody, 2001, Cell. Mol. Life Sci., 58:1461-1474). Later, using total extracts, it was shown that *M. tuberculosis* CD1 antigen presentation is regulated through TLR-2 which responds to known TLR-2 agonists produced by bacterial pathogens and used as total or partially purified lipid extracts (Roura-Mir, et al., 2005, J. Immunol. 175: 1758-1766). Since the effector molecules were not identified in this work, it is not known if the same components isolated in the work by Moody, et al., were the same effector molecules in the work by Roura-Mir, et al.

What is needed are compositions and methods for the modulation of immune responses mediated by TLRs and which are useful for conducting scientific research into TLR-mediated immune system functions, selecting for inhibitors and activators of TLR-mediated immunity and for the prevention and/or treatment of diseases and illnesses.

SUMMARY OF THE INVENTION

The present invention relates to the use of various phosphorylated polyprenols for the regulation of the immune response via the Toll-Like Receptor-mediated (modulated) pathway(s). Phosphorylated polyprenols are described in U.S. Pat. No. 6,525,035 to Danilov, et al. In particular, the present invention relates to the use of these compositions for the upregulation of immune responses in animals and other organisms via the TLR pathway. Although the ability of some phosphorylated polyprenols to upregulate components of the adaptive immune response were known before the present invention, the target and mechanism of the compounds and pharmaceuticals of the present invention was unknown. Furthermore, the ability of these compounds and pharmaceutical compositions based on these compounds to affect TLR activity or mediate their effects through TLRs was also unknown. Further still, since the activation and/or mediation of TLR-mediated immune activity is independent of other forms of immune responses; the activation of the TLR pathway by the compounds of the present invention is novel and non-obvious over that already known by those practiced in the art.

Previously, phosphorylated polyprenols were found to exert their activity via the up regulation of the enzyme 2'-5'-oligoadenylate synthetase (2-5A synthetase) and cyclic AMP (cAMP). See, for example, Russian patent no. 2,177, 788 to Danilov, et al. In that patent, it was shown that the treatment with phosphorylated polyprenols resulted in a 5.7-fold increase of 2-5A synthetase in J-96 cell cultures and a 2.9-fold increase for L-929 cell cultures. 2-5A synthetase is known to play a critical role in IFN-γ related immune responses. See, for example, Behera, et al., J Biol Chem, 277:25601-25608, 2002; Tilles, et al., Pro Soc Exp Biol Med, 186:70-74, 1987. cAMP is an important secondary messenger in many intracellular pathways including adaptive immune responses and associated Th1-mediated immune responses. See, for example, Plescia, et al., Proc Nat Acad Sci, USA, 72:888-891, 1975; Zhang, et al., J Immunology, 165:1762-1770, 2000. Neither 2-5A synthetase or cAMP are known to be directly involved in TLR-mediated pathways. In fact, some studies have found cAMP to be antagonistic to TLR-mediated pathways. See, for example, Schnurr, et al., Blood, 105:1582-1589, 2005. In that paper, Schnurr, et al., showed that cAMP inhibited TLR-induced IL-12 and IL-27 expression. Thus, phosphorylated polyprenols were also thought to mediate their effects by directly simulating cell proliferation of, especially, Th1 T-cells. Therefore, activation of the innate immune system by these phosphorylated polyprenols, as is taught herein, was both unpredicted and unexpected by those of skill in the art.

Human monocytic cells, including a well-studied THP-1 cell line, have served as a reliable model for studies of the TLR-regulated processes. In this cell line, bacterial cell wall lipopolysaccharide (LPS), a TLR-2 and TLR-4 agonist, was shown to upregulate the IkB kinase complex, which regulates all NF-kB-dependent pathways (Hawiger, et al., 1999, Blood, 94: 1711-1716) and to induce production of cytokines including IL (interleukin)-1a, IL-1b, IL-8 (*Campylobacter jejuni* LPS; Jones, et al., 2003, Inf Immunity, 71: 2626-2633) and TNF-α (*Mycobacterium bovis* BCG, Oliveira, et al., 2001, Mem Inst Oswaldo Cruz, Rio de Janeiro, 96: 973-978). Other cytokines are also known to be expressed depending on the type of agonist used and TLR activated (e.g., IL-12, IL-18 and IL-27). Another known TLR-2 and TLR-4 agonist is biglycan, a small leucine-rich proteoglycan (Shaefer, et al., 2005, J. Clin. Invest. 115: 2223-2233).

Certain patterns of cytokine production have been assigned to T-helper cell Types 1 (Th-1: IL-2, INF-γ, TNF-β) and 2 (Th-2: IL-4, IL-5, IL-10 and IL-13). These two polarized forms of the specific cellular immune response provide a useful model for explaining not only the different types of protection, but also the pathogenic mechanisms of several immunopathological disorders (Del Prete, 1998) although later studies recategorized Th-1 type response as cell-mediated and Th-2 type responses which are humoral (Tausk, et al., 2008, Elkarmi & Hamad, 2007) and concluded that both are adaptive whereas T-cell polarization one way, or the other, is stochastic (Elkarmi & Hamad, 2007).

Consequently, the ability of the compounds of the present invention (phosphorylated polyprenols) to up-regulate the innate immune response or mediate such effects via the TLRs was unknown at the time of the invention. Additionally, since the cytokine profile generated as a result of TLR-mediated induction of the innate immune system ["The TLR signaling through different intracellular molecules . . . leads to a distinct set of proinflammatory gene expressions." (Krishnan, et al., Exp and Mol Med, 39:421-438, 2007)] is different than the cytokine profile generated by, for example, Th1-mediated or Th-2 mediated regulation of the adaptive immune response, the induction of one system can occur independently and be detected independently and in the absence of the activation of the other system. Thus, the induction of the innate immune system by the compounds of the present invention (via, for example, TLRs) is not a component necessarily present in induction of the adaptive immune system by those compounds. Rather, it is an independently effected event that may be induced without the induction of the adaptive immune system.

In this regard, the present invention is related to novel compounds based on the phosphorylated polyprenol architecture and the use of those compounds for the regulation of innate immune system functions for the practice of research and for the treatment of disease. In particular, the compounds of the present invention are useful as activators of the innate immune response via, for example, the activation of TLRs. In this regards, the compounds of the present invention may be used both in vivo and in vitro. In vitro use may be, for example, to as controls on assays to screen for small molecule modulators of TLR activation or inhibition.

For the purposes of this application, the term "innate immune response," "innate immunity" and similar phrases are defined as the portion of the immune system comprising the cells and mechanisms that defend the host from infection by other organisms, in an antigen-non-specific, non-antibody-mediated manner. This means that the cells of the innate system (e.g., dendritic cells, macrophages, mast cells, neutophils, etc., recognize and respond to pathogens in a generic way and, unlike the adaptive immune system (comprising the humoral and adaptive immune responses), it does not confer long-lasting or protective immunity to the host. Innate immune systems provide immediate defense against infection and are responsible for, e.g., the inflammatory response.

Polyprenols and phosphorylated polyprenols are defined by Hemming (Proceedings of the Biochemical Society, Biochem, J., 113:23p-25p, 1969 Prenol Nomenclature (1986) International Union of Pure and Applied Chemistry and International Union of Biochemistry: www.chem.qmu-l.ac.uk/iupac. In this regard, it is contemplated that the present invention also comprises compounds and derivatives based on the phosphorylated polyprenol architecture presented below.

In this regard, the present invention contemplates compositions comprising, 1) polyprenol monophosphates of Formula 1:

$$R1-CH_2(R2-CH_2)-C=CH-CH_2-[CH_2-C(CH_3)=CH-CH_2]_n-O-P(=O)(O)_2-R3(R4) \quad (1)$$

wherein R1 and/or R2 and/or R3 and/or R4 are selected from a group consisting of, —H, —OH, —CH₃, hydrocarbons, amino acids, amines, lipids, carbohydrates or sugars and wherein n is an integer from 5-18 inclusive or a salt thereof, and/or 2) polyprenol pyrophosphates of the Formula 2:

$$R1(R2)-C=CH-CH_2-[CH_2-C(CH_3)=CH-CH_2]_m-O-P(=O)(OH)-O-P(=O)(O)_2-R3(R4) \quad (2)$$

wherein R1 and/or R2 and/or R3 and/or R4 are selected from a group consisting of, —H, —OH, —CH₃, hydrocarbons, amino acids, amines, lipids, carbohydrates or sugars and wherein m is an integer from 5-18 inclusive or a salt thereof. The invention also provides pharmaceutical compositions comprising the compounds of the invention as well as therapeutic methods for using the compositions.

In another embodiment, one or both of R1 and R2 are not methyl groups (—CH$_3$).

It will be appreciated by those skilled in the art that polyprenes possess double bonds which may exist in cis, or trans configurations. It is to be understood that the present invention encompasses any stereoisomeric form of the polyenes as well as mixtures thereof, which possess the useful properties described herein.

The present invention also comprises compounds based on the phosphorylated polyprenol architecture above and wherein the terminal phosphate group is a salt and/or additionally comprises a moiety selected from a group consisting of carbohydrates, lipids or metals or salts or acids thereof.

Compounds based on the phosphorylated polyprenols of the present invention (Formula 1 and/or Formula 2) with the modifications listed in the preceding two paragraphs above are herein known as "derivatives of Formula 1," "derivatives of Formula 2," "derivatives," "compound(s) of the present invention," the "Substance" or the like.

The synthesis of derivatives of the phosphorylated polyprenols of Formula 1 and Formula 2 are known in the art. For example, U.S. Pat. No. 4,059,641, entitled "Polyprenyl Derivatives" to Mishima, et al., which is herein incorporated by reference, teaches the synthesis of these and other polyprenol derivatives. Likewise, Maltsev, et al., (Russian Journal of Biological Chemistry, 27:449-452, 2001) teach the synthesis of dolichyl and polyprenyl sulfates. Likewise, Rudney (Proceedings of the Biochemical Society, Biochem J., 128:13 p-14 p, 1972) discloses the biosynthesis of polyprenyl derivatives of p-hydroxybenoate. Fairlamb, et al., describes modification of pharnesyl diphosphate with sulphonyl moiety (Bioorg Chemi 2003, 31:80-97) which method may be applied to phosphorylated polyprenols.

These derivatives of phosphorylated polyprenols described above are known in the art to function similarly. For example, U.S. Pat. No. 4,059,641 (the '641 patent) to Mishma, et al., teaches that the derivatives of the '641 patent all express anti-ulcer activity, albeit to different degrees of activity (see, Table 1 of U.S. Pat. No. 4,059,641, for example).

In one embodiment, the compound(s) of the present invention comprises about 50 wt % (weight percent), 75 wt %, 90 wt %, 95 wt %, about 99 wt %, about 99.5 wt %, about 99.9, wt % or greater of one or more of the derivatives given above. In another embodiment, the compound of the present invention comprises about 95 wt %, about 99 wt %, about 99.5 wt %, about 99.9 wt % or greater of one of the derivatives given above. In another embodiment, when comprising a pharmaceutically acceptable carrier, the compound of the present invention comprises up to about 99.9% of one or more of the compositions of the present invention. In another embodiment, when comprising a pharmaceutically acceptable carrier, the compound(s) of the present invention comprises not less than 90 wt %, 95 wt %, 99 wt % or 99.9 wt % of one or more of the compositions of the present invention.

Pharmaceutical compositions comprising the compound(s) of the present invention may be used, for example, to modulate or stimulate the innate immune system of an animal or other organism. In this regard, the pharmaceutical composition comprising of an effective immuno-modulatory (of the innate immune system) amount of one or more compounds of the present invention is administered to an animal (preferably a mammal) or other organism (herein collectively referred to as the "subject" or subjects") in need of such treatment.

In another embodiment, pharmaceutical compositions comprising the compound(s) of the present invention may be used, for example, to modulate or stimulate the up regulation or activation of one or more TLRs of an animal or other organism. In this regard, the pharmaceutical composition comprising an effective TLR-modulatory amount of one or more compound(s) of the present invention is administered to an animal (preferably a mammal) or other organism (herein collectively referred to as the "subject" or "subjects") in need of such treatment. The phrase "cause to be administered" refers to one person or entity instructing another person or entity to administer the agent(s) of the present invention via, for example, direct communication of by writing a prescription.

The present invention also contemplates that the compounds and compositions of the invention are used, for example, to screen for small molecule inhibitors and activators of TLR-mediated signaling or activity. For example, the compounds and compositions of the present invention may be used as positive controls in an assay system designed to screen for such small molecules effective in modulating TLR-mediated signaling or activity.

Furthermore, it is contemplated that the compounds and compositions of the present invention are useful to identify other receptors that may interact with the compound and compositions of the present invention. In this regard, the compounds of the present invention may be tagged with molecules for detection via biochemical or biological means. For example, fluorescent tags may be used for detection via fluorescent microscopy or flow cytometry. Electron dense tags may be used for detection via electro microscopy. Antibodies may be generated to the compounds of the present invention (by using haptens, if necessary) so that molecules that bind to the compounds of the present invention can be isolated and identified.

Still further, the compounds and compositions of the present invention may be administered to research animals to investigate modulation of the innate immune system and the modulation of signaling via the TLRs.

In regards to the teachings of this specification, in one embodiment, the present invention contemplates a method of modulating the response of Toll-like Receptors (TLR) in a subject, said method comprising administering to or causing to be administered to the subject a pharmaceutical composition comprising at least one polyprenol phosphate selected from the general formulas:

(1)

(2)

wherein R1 and/or R2 and/or R3 and/or R4 are selected from a group consisting of, —H, —OH, —CH$_3$, hydrocarbons, amino acids, amines, lipids, carbohydrates or sugars and wherein m or n is an integer from 5-18 or a salt thereof.

In another embodiment, the present invention contemplates that the pharmaceutical composition additionally used in a method of modulating the response of Toll-like Receptors (TLR) in a subject comprises a pharmaceutically acceptable carrier.

In yet another embodiment, the present invention contemplates compound(s) of the present invention used in a method of modulating the response of Toll-like Receptors (TLR) in a subject, wherein n is 8, 9, 10, 11, 12, or 13 in greater than 50% of the polyprenol monophosphates.

In still yet another embodiment, the present invention contemplates compound(s) of the present invention used in a method of modulating the response of Toll-like Receptors (TLR) in a subject, wherein m is 8, 9, 10, 11, 12, or 13 in greater than 50% of the polyprenol pyrophosphates.

In still yet another embodiment, the present invention contemplates compound(s) of the present invention used in a method of modulating the response of Toll-like Receptors (TLR) in a subject, wherein the weight percent of polyprenol monophosphates is greater than the weight percent of the polyprenol pyrophosphates.

In still yet another embodiment, the present invention contemplates compound(s) of the present invention used in a method of modulating the response of Toll-like Receptors (TLR) in a subject, wherein the weight percent of polyprenol monophosphates is not more than about 2 times greater than the weight percent of the polyprenol pyrophosphates.

In still yet another embodiment, the present invention contemplates compound(s) of the present invention used in a method of modulating the response of Toll-like Receptors (TLR) in a subject, wherein the weight percent of polyprenol monophosphates is not more than about 4 times greater than the weight percent of the polyprenol pyrophosphates.

In still yet another embodiment, the present invention contemplates compound(s) of the present invention used in a method of modulating the response of Toll-like Receptors (TLR) in a subject, wherein the weight percent of polyprenol monophosphates is not more than about 5 times greater than the weight percent of the polyprenol pyrophosphates.

In still yet another embodiment, the present invention contemplates compound(s) of the present invention used in a method of modulating the response of Toll-like Receptors (TLR) in a subject, wherein the weight percent of polyprenol monophosphates is not more than about 10 times greater than the weight percent of the polyprenol pyrophosphates.

In still yet another embodiment, the present invention contemplates compound(s) of the present invention used in a method of modulating the response of Toll-like Receptors (TLR) in a subject, wherein the weight percent of polyprenol monophosphates is not more than about 20 times greater than the weight percent of the polyprenol pyrophosphates.

In still yet another embodiment, the present invention contemplates compound(s) of the present invention used in a method of modulating the response of Toll-like Receptors (TLR) in a subject, wherein n is 11 in at least 80% of the polyprenol monophosphates present.

In still yet another embodiment, the present invention contemplates compound(s) of the present invention used in a method of modulating the response of Toll-like Receptors (TLR) in a subject, wherein m is 11 in at least 80% of the polyprenol pyrophosphates present.

In still yet another embodiment, the present invention contemplates compound(s) of the present invention used in a method of modulating the response of Toll-like Receptors (TLR) in a subject, wherein the weight percent of polyprenol monophosphates is not less than about 10 times greater than the weight percent of the polyprenol pyrophosphates.

In still yet another embodiment, the present invention contemplates compound(s) of the present invention used in a method of modulating the response of Toll-like Receptors (TLR) in a subject, wherein the weight percent of polyprenol monophosphates is not less than about 20 times greater than the weight percent of the polyprenol pyrophosphates.

In still yet another embodiment, the present invention contemplates compound(s) of the present invention used in a method of modulating the response of Toll-like Receptors (TLR) in a subject, wherein the Toll-like receptors are selected from a group consisting of TLR-2 and TLR-4.

In still yet another embodiment, the present invention contemplates compound(s) of the present invention used in a method of modulating the response of Toll-like Receptors (TLR) in a subject, wherein the activation of TLR is identified by the expression of a cytokine profile comprising interleukin-12, interleukin-18 and interferon-gamma.

In still yet another embodiment, the present invention contemplates compound(s) of the present invention used in a method of modulating the response of Toll-like Receptors (TLR) in a subject, wherein the cytokine profile further comprises TNF alpha, IL-1 beta, IL-6, IL-8 and IL-27.

In still yet another embodiment, the present invention contemplates compound(s) of the present invention used in a method of modulating the response of Toll-like Receptors (TLR) in a subject, wherein R1 and/or R2 and/or R3 and/or R4 are different moieties.

In still yet another embodiment, the present invention contemplates compound(s) of the present invention used in a method of modulating the response of Toll-like Receptors (TLR) in a subject, wherein at least two of R1 and/or R2 and/or R3 and/or R4 are the same moieties.

In still yet another embodiment, the present invention contemplates compound(s) of the present invention used in a method of modulating the response of Toll-like Receptors (TLR) in a subject, wherein one or both R1 and R2 are not —CH$_3$.

In regards to the teachings of this specification, in one embodiment, the present invention contemplates a method of modulating the response of innate immune system in a subject, said method comprising administering to or causing to be administered to the subject a pharmaceutical composition comprising at least one polyprenol phosphate selected from the general formulas:

(1)

(2)

wherein R1 and/or R2 and/or R3 and/or R4 are selected from a group consisting of, —H, —OH, —CH$_3$, hydrocarbons, amino acids, amines, lipids, carbohydrates or sugars and wherein m or n is an integer from 5-18 or a salt thereof.

In another embodiment, the present invention contemplates that the pharmaceutical composition additionally used in a method, wherein pharmaceutical composition additionally comprises a pharmaceutically acceptable carrier.

In yet another embodiment, the present invention contemplates compound(s) of the present invention used in a method, wherein n is 8, 9, 10, 11, 12, or 13 in greater than 50% of the polyprenol monophosphates.

In still yet another embodiment, the present invention contemplates compound(s) of the present invention used in a method, wherein m is 8, 9, 10, 11, 12, or 13 in greater than 50% of the polyprenol pyrophosphates.

In still yet another embodiment, the present invention contemplates compound(s) of the present invention used in a method, wherein the weight percent of polyprenol monophosphates is greater than the weight percent of the polyprenol pyrophosphates.

In still yet another embodiment, the present invention contemplates compound(s) of the present invention used in a method, wherein the weight percent of polyprenol monophosphates is not more than about 2 times greater than the weight percent of the polyprenol pyrophosphates.

In still yet another embodiment, the present invention contemplates compound(s) of the present invention used in a method, wherein the weight percent of polyprenol monophosphates is not more than about 4 times greater than the weight percent of the polyprenol pyrophosphates.

In still yet another embodiment, the present invention contemplates compound(s) of the present invention used in a method, wherein the weight percent of polyprenol monophosphates is not more than about 5 times greater than the weight percent of the polyprenol pyrophosphates.

In still yet another embodiment, the present invention contemplates compound(s) of the present invention used in a method, wherein the weight percent of polyprenol monophosphates is not more than about 10 times greater than the weight percent of the polyprenol pyrophosphates.

In still yet another embodiment, the present invention contemplates compound(s) of the present invention used in a method, wherein the weight percent of polyprenol monophosphates is not more than about 20 times greater than the weight percent of the polyprenol pyrophosphates.

In still yet another embodiment, the present invention contemplates compound(s) of the present invention used in a method, wherein n is 11 in at least 80% of the polyprenol monophosphates present.

In still yet another embodiment, the present invention contemplates compound(s) of the present invention used in a method, wherein m is 11 in at least 80% of the polyprenol pyrophosphates present.

In still yet another embodiment, the present invention contemplates compound(s) of the present invention used in a method, wherein the weight percent of polyprenol monophosphates is not less than about 10 times greater than the weight percent of the polyprenol pyrophosphates.

In still yet another embodiment, the present invention contemplates compound(s) of the present invention used in a method, wherein the weight percent of polyprenol monophosphates is not less than about 20 times greater than the weight percent of the polyprenol pyrophosphates.

In still yet another embodiment, the present invention contemplates compound(s) of the present invention used in a method, wherein said activation of the innate immune system includes the activation of Toll-Like Receptors.

In still yet another embodiment, the present invention contemplates compound(s) of the present invention used in a method, wherein said Toll-like receptors are TLR-2 and TLR-4.

In still yet another embodiment, the present invention contemplates compound(s) of the present invention used in a method, wherein activation of TLR is identified by the expression of a cytokine profile comprising interleukin-12, interleukin-18 and interferon-gamma.

In still yet another embodiment, the present invention contemplates compound(s) of the present invention used in a method, wherein the cytokine profile further comprises TNF alpha, IL-1 beta, IL-6, IL-8 and IL-27.

In still yet another embodiment, the present invention contemplates compound(s) of the present invention used in a method, wherein R1 and/or R2 and/or R3 and/or R4 are different moieties.

In still yet another embodiment, the present invention contemplates compound(s) of the present invention used in a method, wherein at least two of R1 and/or R2 and/or R3 and/or R4 are the same moieties.

In still yet another embodiment, the present invention contemplates compound(s) of the present invention used in a method, wherein one or both R1 and R2 are not —CH$_3$.

DETAILED DESCRIPTION OF THE INVENTION

Formulations and Uses of the Compounds of the Present Invention

The inventors have discovered that compositions described in U.S. Pat. No. 6,525,035 (which is incorporated herein by reference) and variations (including both mono- and pyrophosphorylated variations) described herein have utility for the activation and modulation of the innate immune response in general and the activation and modulation of TLRs in particular. In this regard, the compounds of the present invention may be used for the treatment and prevention of a wide range of infectious diseases caused by fungi, bacteria, viruses or used in oncologic pathology, for control of the innate immune response component of allergic or inflammatory diseases and for enhancement of action of vaccines when used wholly or partly as an adjuvant, etc.

Specific and preferred values listed below are for illustration only; they do not exclude other defined values or other values within defined ranges for the radicals and substituents.

The polyprenol phosphates and pyrophosphates can be prepared from polyprenol using procedures similar to those known in the art. See, for example, V. N. Shibaev, and L. L. Danilov, Biochem. Cell Biol., 1992, 70, 429-437 and European Patent Application Number 0 350 801.

Polyprenols can be isolated from natural sources using procedures similar to those described by, for example, Danilov L. L. and Shibaev V. N. (1991): Phosphopolyprenols and their glycosyl esters: chemical synthesis and biochemical application, Atta-ur-Rahman (ed); Studies in natural products chemistry, Elsevier, Amsterdam—Oxford—New York—Tokyo, 8, 63-114; T. Choinacki, Acta. Chem. And Biochem Polonica, 1984, 21, 3-25; and F. Takaki et al., European Patent Application 0 166 436 A2.

Administration of the compounds as salts may be appropriate. Examples of acceptable salts include alkali metal (for example, sodium, potassium or lithium) or alkaline earth metal (for example, calcium) salts, however, any salt that is non-toxic and effective when administered to the animal or other organism being treated is acceptable.

Acceptable salts may be obtained using standard procedures well known in the art, for example, by reacting a sufficiently acidic compound with a suitable base affording a physiologically acceptable anion.

The compositions of the invention can be formulated as pharmaceutical compositions and administered to an animal host (or other organism) such as a human patient in a variety of forms adapted to the chosen route of administration, i.e., orally or parenterally (not via the digestive canal), by intravenous (i.v.), intramuscular (i.m.), topical or subcutaneous routes, for example.

Thus, the present compound(s) may be systemically administered, e.g., orally, in combination with a pharmaceutically acceptable vehicle such as an inert diluent or an assimilable edible carrier. They may be enclosed in hard or soft shell gelatin capsules, may be compressed into tablets or may be incorporated directly with the food of the patient's diet. For oral therapeutic administration, the active compound(s) may be combined with one or more excipients and used in the form of ingestible tablets, buccal tablets, troches, capsules, elixirs, suspensions, syrups, wafers and the like. Such compositions and preparations should contain at least 0.1% of active compound by weight percent. The percentage of the compositions and preparations may, of course, be varied and may conveniently be between about 2 to about 60% of the weight of a given unit dosage form. The amount of active compound(s) in such therapeutically useful compositions is such that an effective dosage level will be obtained. When administered orally, the compositions of the invention can preferably be administered in a gelatin capsule.

The tablets, troches, pills, capsules and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills or capsules may be coated with gelatin, wax, shellac or sugar and the like. A syrup or elixir may contain the active compound(s), sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound(s) may be incorporated into sustained-release preparations and devices.

The compositions of the invention may also be administered intravenously or intraperitoneally by infusion or injection. Solutions of the active composition can be prepared in water, optionally mixed with a nontoxic surfactant. Dispersions can also be prepared in glycerol, liquid polyethylene glycols, triacetin and mixtures thereof and in oils. Under ordinary conditions of storage and use these preparations may contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active composition in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the present compositions may be applied in pure form, i.e., liquids. However, it will generally be desirable to administer them to the skin as compositions or formulations in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Additives such as fragrances and additional antimicrobial agents can be added to optimize the properties for a given use. The resultant liquid compositions can be applied from absorbent pads, used to impregnate bandages and other dressings or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps and the like for application directly to the skin of the user.

Examples of useful dermatological compositions which can be used to deliver the compounds and derivatives of Formula 1 and/or Formula 2 to the skin are known to the art;

for example, see Jacquet, et al., (U.S. Pat. No. 4,608,392), Geria (U.S. Pat. No. 4,992,478), Smith, et al., (U.S. Pat. No. 4,559,157) and Wortzman (U.S. Pat. No. 4,820,508), all of which are incorporated herein by reference.

Useful dosages of the compounds of Formula 1 and/or Formula 2, or derivatives derived there from and described herein, can be determined by comparing their in vitro activity and in vivo activity in animal models. Methods for the extrapolation of effective dosages in mice and other animals to humans are known to the art; for example, see U.S. Pat. No. 4,938,949, which is incorporated herein by reference.

Generally, the concentration of the compositions of the invention in a liquid composition, such as a lotion, will be from about 0.1-50 wt % (weight percent), preferably from about 0.5-5 wt %. The concentration in a semi-solid or solid composition such as a gel or a powder will be about 0.1-5 wt %, preferably about 0.5-2.5 wt %.

The amount of the composition required for use in treatment will vary not only with the particular salt selected but also with the route of administration, the nature of the condition being treated and the age and condition of the patient and will be ultimately at the discretion of the attendant physician or clinician.

In general, however, a suitable average dose will be in the range of from about 0.25 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compositions are conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably about 1 to 50 µM, most preferably, about 2 to about 30 µM. This may be achieved, for example, by the intravenous injection of a 0.05 to 5 wt % solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Although the present invention is not limited to any specific theory, it is believed that the compositions of the invention are poly-functional both at the cellular and at the organism levels. At the cellular level, they are incorporated into or associated with the cellular membranes, enhancing their permeability and changing membrane properties. They also normalize and activate processes of cell surface glycoprotein biosynthesis, normalizing cell reproduction intracellular and, as a result, inter-tissue interactions. In the organism on the whole they normalize, augment or activate immune system functioning or modulate it through mechanisms associated with, for example, Toll (TLR)-receptor signaling and/or through CD-1 (family of lipid recognition glycoproteins) interactions or improve the function of individual organs, enhances blood generation function and facilitate tissue regeneration.

The compositions of the invention are useful for prevention, treatment and liquidation of consequences of diseases involving an innate immune response, including, but not limited to, viral, chlamydial, bacterial, oncology, liver, gastrointestinal, urologic and reproductive system, immune system, wounds, burns and stresses.

Following i.m. (intramuscular) administration, the compositions of the invention enter the blood stream within about 10-15 minutes and reach a maximum concentration in the blood within one hour of administration, at which point they can be found throughout the circulatory related organs.

The antiviral activity of the compositions of the invention can be determined using assays that are known in the art or can be determined using assays similar to those described in the following examples.

The compositions of the invention can be used, for example, for the treatment of animal diseases caused by numerous viruses including distemper virus (DV), canine enteritis (parvo, rota, and corona viruses; CEV), canine infectious hepatitis (CIH), feline infectious gastroenteritis (panleukopenia, FIE), feline infectious rhinotracheitis (agent—herpes virus; FIR), feline infectious enteritis and peritonitis (agent—corona virus, FIP), swine transmissive gastroenteritis (agent—rotavirus; STG), murine ectromelia (ME), cattle leukemia (CL), calf mixed viral infection (agents—parvo, adeno and corona viruses; CMVI), western equestrian encephalomyelitis (WEE), and rabies (RV).

As used in the examples herein, the phrase "compounds of the present invention (Formula 1 and/or Formula 2 and derivatives thereof)" is a composition of the invention wherein the compound(s) of the invention comprise at least 50 wt %, 75 wt %, 90 wt %, 95 wt %, 99 wt %, 99.5 wt % or 99.9 wt % of one or more of the compounds or derivatives described herein not including any additives, excipients or other ingredients that are not. In addition, the phrase "compounds of the present invention (Formula 1 and/or Formula 2 and derivatives thereof)" also encompass any of the phosphorylated polyprenol-based compounds and compositions given herein as well as their stereoisomeric forms.

In this regard, the present invention contemplates compositions comprising, 1) polyprenol monophosphates of Formula 1:

$$R1\text{-}CH_2(R2\text{-}CH_2)\text{---}C\text{=}CH\text{---}CH_2\text{---}$$
$$[CH_2\text{---}C(CH_3)\text{=}CH\text{---}CH_2]_n\text{---}O\text{---}P$$
$$(\text{=}O)(O)_2\text{---}R3(R4) \quad (1)$$

wherein R1 and/or R2 and/or R3 and/or R4 are selected from a group consisting of, —H, —OH, —CH$_3$, hydrocarbons, amino acids, amines, lipids, carbohydrates or sugars and wherein n is an integer from 5-18 inclusive or a salt thereof, and/or 2) polyprenol pyrophosphates of the Formula 2:

$$R1(R2)\text{-}C\text{=}CH\text{---}CH_2\text{---}[CH_2\text{---}C(CH_3)\text{=}CH\text{---}$$
$$CH_2]_m\text{---}O\text{---}P(\text{=}O)(OH)\text{---}O\text{---}P(\text{=}O)(O)_2\text{---}$$
$$R3(R4) \quad (2)$$

wherein R1 and/or R2 and/or R3 and/or R4 are selected from a group consisting of, —H, —OH, —CH$_3$, hydrocarbons, amino acids, amines, lipids, carbohydrates or sugars and wherein m is an integer from 5-18 inclusive or a salt thereof. The invention also provides pharmaceutical compositions comprising the compounds of the invention as well as therapeutic methods for using the compositions.

It will be appreciated by those skilled in the art that polyprenes possess double bonds which may exist in cis or trans configurations. It is to be understood that the present invention encompasses any stereoisomeric form of the polyprenes of the present invention as well as mixtures thereof, which possess the useful properties described herein.

Specific and preferred values listed below are for illustration only; they do not exclude other defined values or other values within defined ranges for the radicals and substituents.

A specific composition of the invention is a composition wherein n is at least 6, wherein the polyprenol monophosphate comprises at least 90%, 95%, 99%, 99.5% or 99.9% of the weight of the composition and the polyprenol pyrophosphate comprises less 10% of the weight.

A specific composition of the invention is a composition wherein n is 8, 9, 10, 11, 12 or 13 in greater than 50% of the polyprenol monophosphates.

A specific composition of the invention is a composition wherein m is 8, 9, 10, 11, 12, or 13 in greater than 50% of the polyprenol pyrophosphates.

A specific composition of the invention is a composition wherein the weight percent of polyprenol monophosphates is greater than the weight percent of the polyprenol pyrophosphates.

A specific composition of the invention is a composition wherein the weight percent of polyprenol monophosphates is not more than about 2 times greater than the weight percent of the polyprenol pyrophosphates.

A specific composition of the invention is a composition wherein the weight percent of polyprenol monophosphates is not more than about 4 times greater than the weight percent of the polyprenol pyrophosphates.

A specific composition of the invention is a composition wherein the weight percent of polyprenol monophosphates is not more than about 5 times greater than the weight percent of the polyprenol pyrophosphates.

A specific composition of the invention is a composition wherein the weight percent of polyprenol monophosphates is not more than about 10 times greater than the weight percent of the polyprenol pyrophosphates.

A specific composition of the invention is a composition wherein the weight percent of polyprenol monophosphates is not more than about 20 times greater than the weight percent of the polyprenol pyrophosphates.

A specific composition of the invention is a composition wherein n is 10 in at least 80% of the polyprenol monophosphates present.

A specific composition of the invention is a composition wherein m is 10 in at least 80% of the polyprenol pyrophosphates present.

A specific composition of the invention is a composition wherein n is 10 in at least 80% of the polyprenol monophosphates present, and m is 10 in at least 80% of the polyprenol pyrophosphates present.

A specific composition of the invention is a composition wherein n is 10 in at least 80% of the polyprenol monophosphates present, m is 10 in at least 80% of the polyprenol pyrophosphates present, and the weight percent of polyprenol monophosphates is about 10 times greater than the weight percent of the polyprenol pyrophosphates.

A specific composition of the invention is a composition wherein n is 10 in at least 90% of the polyprenol monophosphates present.

A specific composition of the invention is a composition wherein m is 10 in at least 90% of the polyprenol pyrophosphates present.

A specific composition of the invention is a composition wherein n is 10 in at least 90% of the polyprenol monophosphates present, and m is 11 in at least 90% of the polyprenol pyrophosphates present.

A specific composition of the invention is a composition wherein n is 10 in at least 90% of the polyprenol monophosphates present, m is 10 in at least 90% of the polyprenol pyrophosphates present, and the weight percent of polyprenol monophosphates is about 10 times greater than the weight percent of the polyprenol pyrophosphates.

The target and the mechanism of effect that can define utility of the compositions of the invention can be determined using assays that are known in the art or can be determined using assays similar to those described in the following examples.

Applicant has discovered certain compositions that are useful for the prevention and/or treatment of diseases, including viral, chlamidial, bacterial related diseases, oncology related diseases, diseases related to the liver, gastrointestinal, urologic and reproductive systems and diseases related to the function of the immune system. In this regard, the present invention contemplates that the compositions of the present invention are also effective in the treatment of wounds, burns, allergic diseases, and stresses and are useful for medical (human), veterinary and agricultural applications. The pyrophosphate containing compositions of the invention have improved solubility compared to related known compositions and, as a result, demonstrate improved levels of activity against certain diseases.

In particular, it is contemplated that the compounds of the present invention are effective in the modulation (i.e., activation and regulation) of the innate immune system through, for example, interactions involving (directly or indirectly) toll-like receptors (TLR).

Toll-Like Receptors and Innate Immunity

The invention also provides a method for inducing or modulating an innate immune response and/or a TLR-mediated immune response effect in an animal comprising administering to an animal in need of such treatment, an effective amount of a composition of the comprising at least one compound of the present invention. As used herein "animal" includes, for example, mammals (e.g., a dog, cow, cat or human), birds (e.g., poultry) and other animals (fish, insects etc.) that can effectively be treated with the compositions of the invention. In this regard, TLRs are highly conserved molecules in the animal kingdom. In fact, the compounds of the present invention have been shown to be effective in bees.

As used in the examples herein, the phrase "compounds of the present invention (Formula 1 and/or Formula 2 and derivatives thereof)" is a composition of the invention wherein the compound(s) of the invention comprise at least 50 wt %, 75 wt %, 90 wt %, 95 wt %, 99 wt %, 99.5 wt % or 99.9 wt % of one or more of the compounds or derivatives described herein not including any additives, excipients or other ingredients. In addition, the phrase "compounds of the present invention (Formula 1 and/or Formula 2 and derivatives thereof)" also encompass any of the phosphorylated polyprenol-based compounds and compositions given herein as well as their stereoisomeric forms. In this regard, it will be appreciated by those skilled in the art that polyprenes possess double bonds which may exist in cis or trans configurations. It is to be understood that the present invention encompasses any stereoisomeric form of the polyprenes of the present invention as well as mixtures thereof, which possess the useful properties described herein.

The target and the mechanism of effect that can define utility of the compositions of the invention can be determined using assays that are known in the art or can be determined using assays similar to those described by means of the following non-limiting the following examples.

EXEMPLIFICATION

As used in the examples hereinbelow, "the Substance" is a composition of the present invention wherein n is 11 in at least 80% of the polyprenol monophosphates present, m is 11 in at least 80% of the polyprenol pyrophosphates present, and the weight percent of polyprenol monophosphates is about 10 times greater than the weight percent of the polyprenol pyrophosphates.

Example 1: Induction of Biosynthesis of mRNA for Cytokines in THP-1 Cell Culture The compound(s) of Formula 1 and Formula 2 and derivatives thereof of the present invention are effective in inducing cytokines characteristic of an immune response.

THP-1 monocyte cell culture was grown at 37° C., 5% $CO_2$ in RPMI-1640 supplemented with 10% Fetal Bovine Serum and 1% Antibiotic-Antimycotic (all from Invitrogen, Carlsbad, Calif.).

A representative phosphorylated compound of the present invention (as described in U.S. Pat. No. 6,525,035, which is herein incorporated by reference: "Substance") was obtained from Sass & Sass, Inc. (Oak Ridge, Tenn.). Nicotine and Taq polymerase were purchased from Sigma Chemical Co (St. Lois, Mo.), cytokine MessageScreen Kit Th1 and Th2 primer kits were from Biosource, fluo-3 dye was from Molecular Probes (Eugene, Oreg.).

Figure 1:
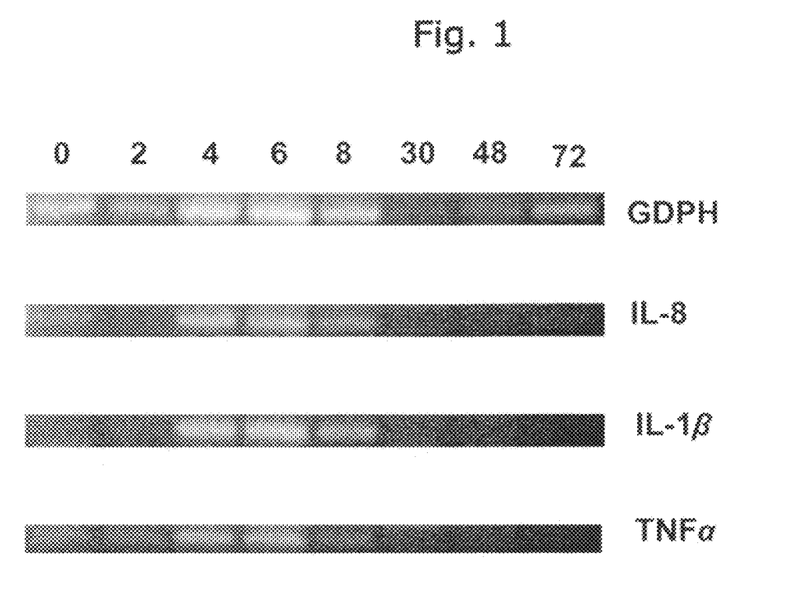
FIG. 1 is a photograph of an agarose gel loaded with PCR-amplified fragments of cDNA copies from cytokine mRNA illustrating cytokine mRNA transcript kinetics induced by the treatment of THP-1 cell with a compound of the present invention (e.g., see, Example 1) over 72 hours. Treatment of the cells with a compound of the present invention led to the increase in abundance of the mRNA transcripts of TNFα, IL-1β, and IL-8 relative to the transcripts of constitutively expressed gene of glyceraldehyde-3-phosphate dehydrogenase (GDPH).
Figure 2:
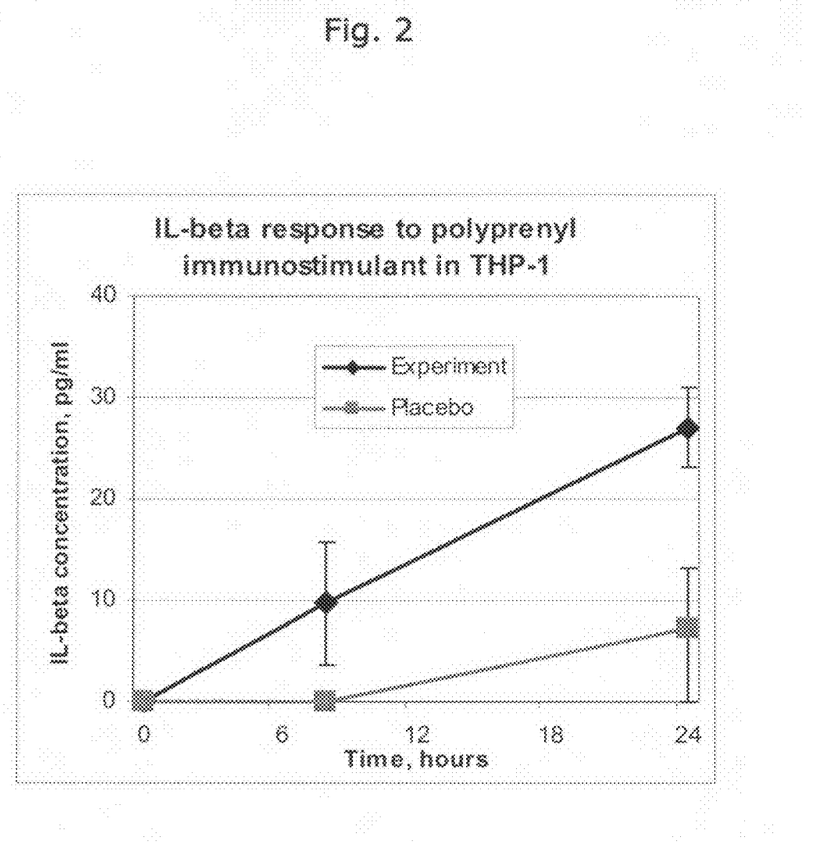
FIG. 2 is a graph showing results of measurement of IL-1β in cell medium by ELISA over 24 hours after the exposure and indicating that treatment of THP-1 cells with the Substance leads to the increase of IL-1β.

Effect of the Substance on cytokine transcription was assessed by RT-PCR at 0, 2, 4, 6, 8, 30, 48 and 72 hours after $10^7$ THP-1 cells in 30 ml of growth medium were supplemented with 200 μg of the Substance. The cells responded to the addition of the Substance with an increase in levels of mRNA of IL-1β, IL-8 and TNFα in two hours after the addition, and mRNA specific levels peaked at 4 to 8 hours (FIG. 1). After 48 hours, the transcripts were no longer observed (FIG. 1). This finding pointed out to potential similarity of the pathway of monocyte induction by a compound of the present invention with monocyte/macrophage induction by LPS (lipopolysaccharide), which upregulates transcription and expression of genes for IL-1 beta, TNF-alpha, IL-6, IL-8 and through interaction with TLR4 receptors (Guha and Mackman, 2001, Cell. Signalling, 13: 85-94). This upregulation is believed to be NF-kappaB and MEK-ERK1/2-dependent (ibid). The Substance did not induce mRNA of IL-6, IL-2, IL-13 or IL-12 p 40 nor was mRNA for these cytokines present in resting THP-1 cells. We observed a weak constitutive transcription of IL-8 and TNF-alpha in the THP-1 cell line, which is in agreement with reports of the presence in resting THP-1 cells of low levels of IL-8 (Bagui, et al., 1999) and of TNFa mRNA (Lagoumintzis, et al., 2003, Inf Immunity, 71: 4614-4622). A 500-800-fold induction of IL-8 production in THP-1 cells by LPS from oral microorganisms has been reported (Baqui, et al., 1999). However, in the THP-1, LPS also stimulated production of IL-6 and IL12 p 40 (Murthy, et al., 2000, Inf Immunity, 68: 6663-6669), mRNA for which were not upregulated by polyprenyl.

Kinetics of mRNA biosynthesis upregulation exhibited sharp peaks at 4-8 hours, after which cytokine mRNA concentration declined (FIG. 1). In LPS-stimulated THP-1 cultures, levels of cytokines also abruptly increased in the first 20 hours post stimulation, and except for the levels of TNF-alpha which peaked at 2 h and declined after 72 h, level of IL-1b remained stable over 160 hours (Murthy, et al., 2000, Inf Immunity, 68: 6663-6669) which may be due to temporal stability of the cytokines.

The preceding experiment demonstrates the compounds of the present invention are effective in inducing an immune response similar but not identical to LPS.

Example 2: Treatment of THP-1 Cells with the Substance Leads to Biosynthesis of Proinflammatory Cytokines TNF-Alpha and IL-1β

This Example shows that the compound(s) of Formula 1 and Formula 2 and derivatives effect the biosynthesis of proinflammatory cytokines TNF-alpha and IL-1-beta.

THP-1 monocyte cell culture was grown at 37° C., 5% $CO_2$ in RPMI-1640 supplemented with 10% Fetal Bovine Serum and 1% Antibiotic-Antimycotic (all from Invitrogen, Carlsbad, Calif.).

A representative phosphorylated compound of the present invention (as described in U.S. Pat. No. 6,525,035, which is herein incorporated by reference: "Substance") was obtained from Sass & Sass, Inc. (Oak Ridge, Tenn.). ELISA Ready-Set-Go kit for TNF-α was from eBiosciences and Human IL-1β ELISA Kit Opta EIA was from BD Biosciences (both companies from San Diego, Calif.). Signal readout was carried out a Molecular Devices plate reader, and the results were processed by the manufacturer-supplied software.

Cells were grown to a density of $1.5$-$2 \cdot 10^6$ cells/ml, harvested by a low-speed centrifugation, resuspended in the fresh growth medium to a density of $2 \cdot 10^6$ cells/ml and incubated at 37° C., 5% $CO_2$ for 3 hours. Two hundred μg/ml of the Substance was added to cells in three wells; cells in three control wells we supplemented with placebo, a 0.7% n-butanol solution in water. Duplicate aliquots were taken for analysis immediately after the addition of the substances and after 7 and 24 hours and analyzed for the presence of IL-1β according to manufacturer's instructions except that we used 3×200 μl of the analyte per well. For the analysis of TNF-α, duplicate aliquots were taken immediately after the addition of the substances and after 3.5 and 8 hours and analyzed for the presence of cytokine according to manufacturer's instructions except that we used 3×200 μl of the analyte per well.

The preceding experiment demonstrates the compounds of the present invention are effective in inducing the biosynthesis of proinflammatory cytokines TNF-alpha and IL-1β.

Example 3: Induction of $Ca^{2+}$ Ion Transients

This experiment demonstrates that the compounds of the present invention are effective in inducing $Ca^{2+}$ ion transients, which are indicative of the activation of the innate immune system.

The compound(s) of Formula 1 and Formula 2 and derivatives of the present invention are effective in inducing a TLR-mediated immune response as evidenced by induction of $Ca^{2+}$ ion transients. The induction of $Ca^{2+}$ ion transients is representative of NFκB induction by TLR stimulation.

A representative phosphorylated compound of the present invention (as described in U.S. Pat. No. 6,525,035, which is herein incorporated by reference: "Substance") was obtained from Sass & Sass, Inc. (Oak Ridge, Tenn.). THP-1 monocyte, retinoblastoma WERI-Rb1 or hippocampal neurons were maintained as cell cultures. Nicotine was obtained from Sigma Chemical Co (St. Lois, Mo.), fluo-3 dye was from Molecular Probes (Eugene, Oreg.). For the fluorescence emission experiments, THP monocyte cell or WERI- Rb1 retinoblastoma cells from human, immortalized cultures were anchored to the bottom of the poly-D-lysine precoated slide wells by overnight incubation in the growth medium; rat hippocampal neurons were in primary culture and used as grown as a monolayer. The growth medium was replaced with 500 µl Hanks supplemented with 50 µM fluo-3 AM (Molecular Probes, Eugene, Oreg.) from a 6 mM stock in dimethylsulfoxide, DMSO; Aldrich Chemical, Milwaukee, Wis.), and 0.02% Pluronic F-127 (Molecular Probes) followed by the incubation at 37° C. for 2 h. The cells were washed three times with the excess of Hanks saline.

The slide wells with the fluo3-loaded cells were fixed onto the thermostated stage (Bionomics BC-1, Technology 2020) and maintained at 37° C. through the experiment. The dye was excited at 490 nm. The response to light was induced by addition of 10 µl of 0.4% solution of the Substance in 0.5% butanol. The Fluo-3 fluorescence emission was collected by an intensified charge cooled device (CCD) (Quantix, Photometrics). Data were processed using Metamorph software (Universal Imaging, West Chester, Pa.).

Figure 3:
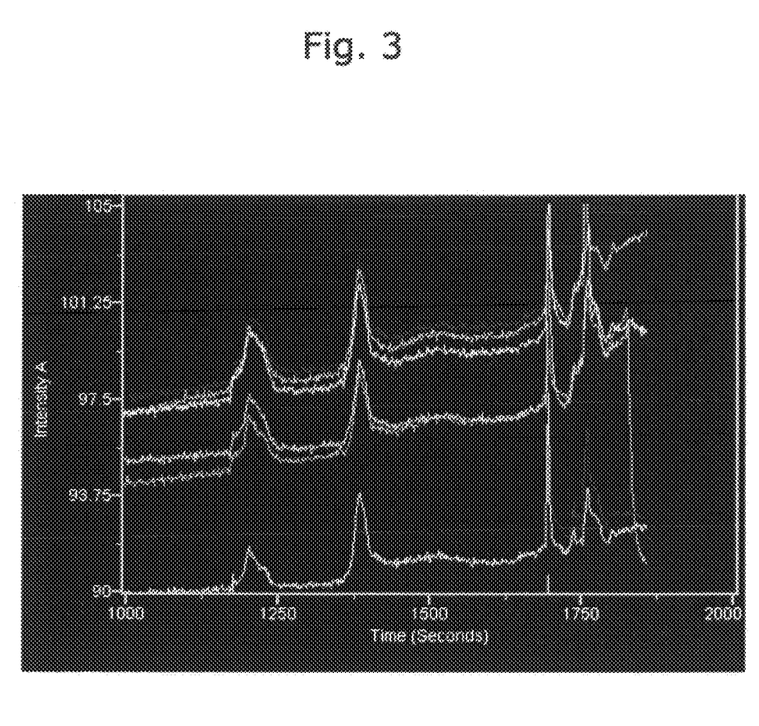
FIG. 3 shows histograms of intensity of fluorescence of Ca-binding dye in six individual hyppocampal neurons (light blue, blue, magenta, yellow, red, green) to which a compound of the present invention was added at 1175 sec, 1375 sec, and 1750 sec demonstrating induction of intracellular Ca$^+$ ion transients in the neurons by a compound of the present invention. Nicotine was added at 1700 sec as a control to prove cellular viability and signaling ability.

The induction of $Ca^{2+}$ ion transients by the Substance is shown in FIG. 3. The addition of 20 µl of the solution to the cells anchored to the well bottom led to an immediate increase in intracellular $Ca^{2+}$ ion concentration. This response is characteristic of the processes linked to NFκB activation (Lewis, 2003, Biochem. Soc. Trans. 31: 925-929, Lilienbaum and Israel, 2003, Mol. Cell. Biol. 23:2680-2698). The NFκB is a part of TLR-triggered responses (Guha and Mackman, 2001, Cell. Signalling, 13: 85-94, Janeway and Medzhitov, 2002, Annu. Rev. Immunol, 20: 197-216).

Thus, we have demonstrated the previously unknown ability of the compounds of the present invention to inducing a TLR-mediated immune response as evidenced by induction of $Ca^{2+}$ ion transients. The induction of $Ca^{2+}$ ion transients is representative of NFκB induction by TLR stimulation.

Example 4: Cytokine Induction Indicative of Activation of the Innate Immune System by Compounds of Formula 1 of the Present Invention is Inhibited by Anti-TLR-2 and Anti-TLR-4 Monoclonal Antibodies Cytokine induction is inhibited by anti-TLR-2 and TLR-4 monoclonal antibodies thereby demonstrating the activation of the innate immune response by the compounds of the present invention.

THP-1 monocyte cell culture was grown at 37° C., 5% $CO_2$ in RPMI-1640 supplemented with 10% Fetal Bovine Serum and 1% Antibiotic-Antimycotic (all from Invitrogen, Carlsbad, Calif.). A representative phosphorylated compound of the present invention (as described in U.S. Pat. No. 6,525,035, which is herein incorporated by reference: "Substance") was obtained from Sass & Sass, Inc. (Oak Ridge, Tenn.). ELISA Ready-Set-Go kit for TNF-α and human anti-TLR-4 and anti-TLR-2 monoclonal antibodies were from eBiosciences (San Diego, Calif.). Signal readout was carried out using a Molecular Devices plate reader, and the results were processed by the manufacturer-supplied software.

Cells were grown to a density of $1.5\text{-}2 \cdot 10^6$ cells/ml, harvested by a low-speed centrifugation, resuspended in the fresh growth medium to a density of $2 \cdot 10^6$ cells/ml and incubated at 37° C., 5% $CO_2$ for 3 hours. Anti-TLR-4 (clone HTA125), anti-TLR-2 (FG purified anti-human TLR2 [TL2.1]) monoclonal antibodies, or their combination, were added to three wells per each substance, and three wells were supplemented with an equal volume of saline (negative control), and the cells were incubated at growth conditions for 60 min. After that, of the Substance was added to cells in three wells to four hundred µg/ml without antibodies (positive control) and to 9 wells with antibodies; cells in three other wells we supplemented with placebo, a 0.7% n-butanol solution in water. Aliquots were sampled for analysis immediately after the addition of the substances and after 3.5 hours and analyzed for the presence of TNF-α according to manufacturer's instructions except that we used 3×200 µl of the analyte per well.

Figure 4:
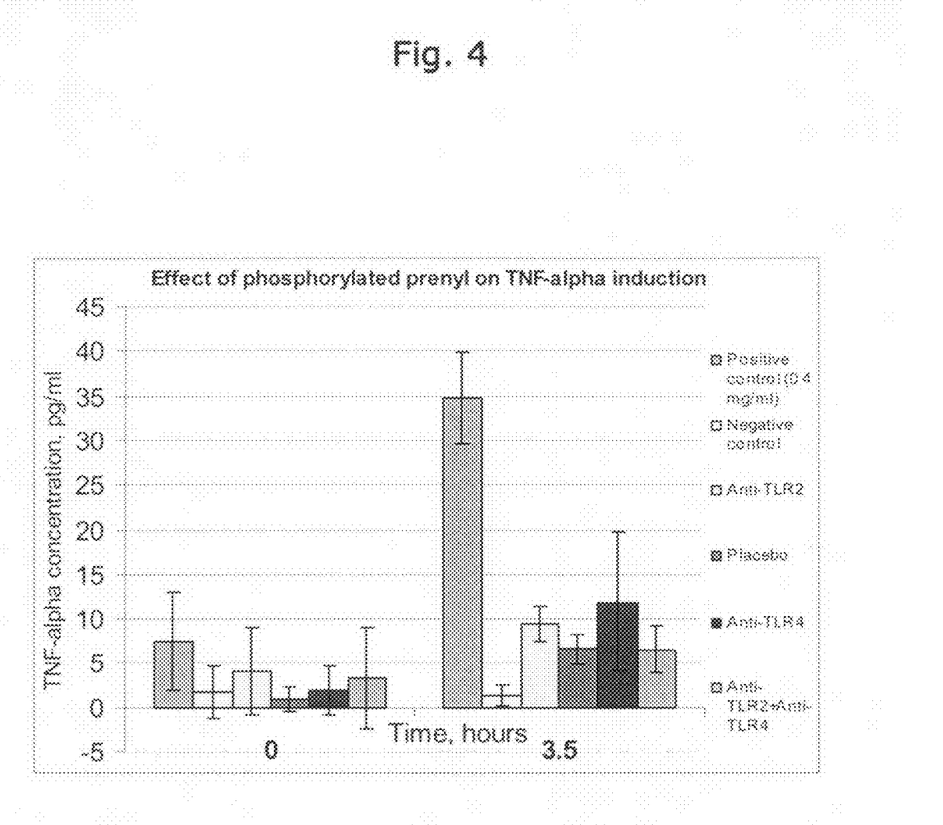
FIG. 4 is a graph demonstrating inhibition of TNF-α induction in phosphorylated polyprenyl-treated THP1 cells by anti-TLR-2, anti-TLR-4, or both, monoclonal antibodies. Concentration of TNF-α was measured in culture media, in triplicates, by ELISA. The experiment demonstrates the involvement of TLR in the activation of an innate immune response to the exclusion of an adaptive immune response.

Results presented in FIG. 4 show that after 3.6 hours, incubation of THP-1 cells with the Substance led to the 7-fold increase of TNF-α in the experimental wells over the control. In the wells supplemented with anti-TLR-2, anti-TLR-4, or both, monoclonal antibodies in addition to the Substance, the increase in TNF-α was not statistically significant. The result indicates that anti-TLR-2, anti-TLR-4, or both monoclonal antibodies inhibit TNF-α induction in THP1 cells. Therefore, TLR-2 and TLR-4 receptors are involved in TNF-α induction by the Substance.

This example has demonstrated the hitherto unknown ability of the compounds of the present invention to activate the innate immune system through TLR by inhibition by blocking the effect with antibodies to TLR-2 and TLR-4.

I claim:

1. A method of activating Toll-like receptors TLR2 and TLR4 in monocytes or macrophages without induction of adaptive immunity, via expression of the cytokine profile comprising INFα, IL-1β, and IL-8, but not IL-6, IL-12, or IL-2, said method comprising contacting monocytes or macrophages with a pharmaceutical composition comprising at least one polyprenol phosphate selected from the formulas (1) or (2):

(1) and (2)

wherein R1 and/or R2 and/or R3 and/or R4 are selected from a group consisting of —H, —OH, hydrocarbons, amino acids, amines, lipids, carbohydrates or sugars and wherein m or n is an integer from 5-18, or a salt thereof.

2. The method of claim 1, wherein pharmaceutical composition additionally comprises a pharmaceutically acceptable carrier.

3. The method of claim 1, wherein n is 8, 9, 10, 11, 12, or 13 in greater than 50% of the polyprenol monophosphates.

4. The method of claim 1, wherein m is 8, 9, 10, 11, 12, or 13 in greater than 50% of the polyprenol pyrophosphates.

5. The method of claim 1, wherein the weight percent of polyprenol monophosphates is greater than the weight percent of the polyprenol pyrophosphates.

6. The method of claim 1, wherein the weight percent of polyprenol monophosphates is not more than about 2 times greater than the weight percent of the polyprenol pyrophosphates.

7. The method of claim 1, wherein the weight percent of polyprenol monophosphates is not more than about 4 times greater than the weight percent of the polyprenol pyrophosphates.

8. The method of claim 1, wherein the weight percent of polyprenol monophosphates is not more than about 5 times greater than the weight percent of the polyprenol pyrophosphates.

9. The method of claim 1, wherein the weight percent of polyprenol monophosphates is not more than about 10 times greater than the weight percent of the polyprenol pyrophosphates.

10. The method of claim 1, wherein the weight percent of polyprenol monophosphates is not more than about 20 times greater than the weight percent of the polyprenol pyrophosphates.

11. The method of claim 1, wherein n is 11 in at least 80% of the polyprenol monophosphates present.

12. The method of claim 1, wherein m is 11 in at least 80% of the polyprenol pyrophosphates present.

13. The method of claim 1, wherein the weight percent of polyprenol monophosphates is not less than about 10 times greater than the weight percent of the polyprenol pyrophosphates.

14. The method of claim 1, wherein the weight percent of polyprenol monophosphates is not less than about 20 times greater than the weight percent of the polyprenol pyrophosphates.

15. The method of claim 1, wherein at least two of R1 and/or R2 and/or R3 and/or R4 are the same moieties.

16. The method of claim 1, wherein one or both R1 and R2 are not —$CH_3$.

\* \* \* \* \*